United States Patent [19]

McQuilkin et al.

[11] Patent Number: 5,219,359
[45] Date of Patent: Jun. 15, 1993

[54] SUTURE APPARATUS

[75] Inventors: Peter H. McQuilkin; Marcus Filshie, both of Notingham, England

[73] Assignee: Femcare Limited, United Kingdom

[21] Appl. No.: 760,929

[22] Filed: Sep. 17, 1991

[30] Foreign Application Priority Data

Sep. 18, 1990 [GB] United Kingdom ................. 9020379

[51] Int. Cl.$^5$ .............................................. A61B 17/00
[52] U.S. Cl. ...................................... 606/232; 602/43
[58] Field of Search .................... 606/232, 148; 623/2; 206/63.3; 602/79, 42, 43

[56] References Cited

U.S. PATENT DOCUMENTS

| 2,199,025 | 4/1940 | Conn | 606/232 |
| 3,541,591 | 11/1970 | Hoegerman | 606/232 |
| 3,976,079 | 8/1976 | Samuels et al. | 606/232 |
| 4,034,850 | 7/1977 | Mandel | 206/63.3 |
| 4,188,953 | 2/1980 | Klieman et al. | 606/158 |
| 4,276,284 | 6/1981 | Brown | 514/8 |
| 4,823,794 | 4/1989 | Pierce | 606/232 |
| 4,938,760 | 7/1990 | Burton et al. | 600/29 |
| 5,000,746 | 3/1991 | Meiss | 602/43 |

FOREIGN PATENT DOCUMENTS

| 2422386 | 4/1978 | France. | |
| 2063675A | 6/1981 | United Kingdom | 606/232 |
| 2114894A | 9/1983 | United Kingdom | 606/232 |
| 2154886A | 9/1985 | United Kingdom | 606/230 |

Primary Examiner—Stephen C. Pellegrino
Assistant Examiner—Gary Jackson
Attorney, Agent, or Firm—Salter, Michaelson & Benson

[57] ABSTRACT

An elongate length of suture is passed through holes in a first small plate (pledget) and holes in a second small plate (pledget), the suture being then tied to retain the two small plates relative to each other and to retain in use tissue between the two small plates (pledgets).

10 Claims, 4 Drawing Sheets

SUTURE APPARATUS

The present invention relates to sutures and more particularly to a suture apparatus for operations such as the STAMEY procedure wherein the suture requires to provide support for the urethra.

The present invention provides a suture apparatus comprising an elongate length of suture, a first pledget comprising a generally rectangular or oval plate of bio-compatible material, the plate being provided with a first and a second hole therethrough, the suture passing through the first and second holes to retain the pledget in position on the suture, thereby providing a first end of said suture exiting from the first hole and a second end of the suture exiting from the second hole, a second pledget comprising a generally rectangular plate of bio-compatible material, the plate being provided with a third and a fourth hole therethrough, the third hole receiving in use the first end of the suture and the fourth hole the second end of the suture in which in use the first end of the suture passes through the third hole and in which the second end of the suture passes through the fourth hole, the two ends of the suture being secured to the first and second pledgets in a predetermined positional relationship with respect to each other.

In a preferred embodiment the suture material is elasticated providing a defined relative movement between the first and second pledgets.

In a preferred embodiment each pledget is radio-opaque being therefore viewable by X-ray.

The suture may be bio-absorbable and one or both of the pledgets may be bio-absorbable.

One or more of the pledgets may be made from a material which allows tissue to grow therein to provide firmer anchorage for the sutures.

Embodiments of the present invention will now be described, by way of example with reference to the accompanying drawings, in which.

Figure 11:
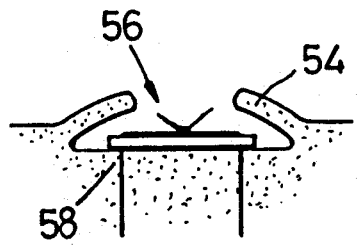
Figure 12:
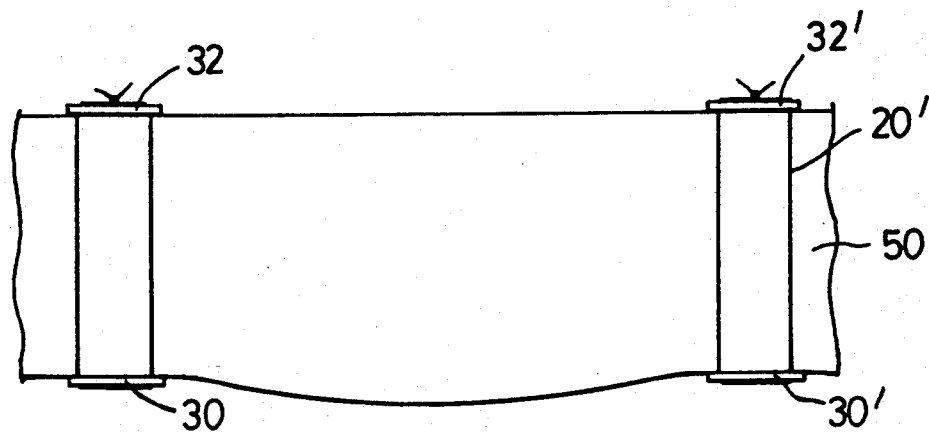
Figure 13:
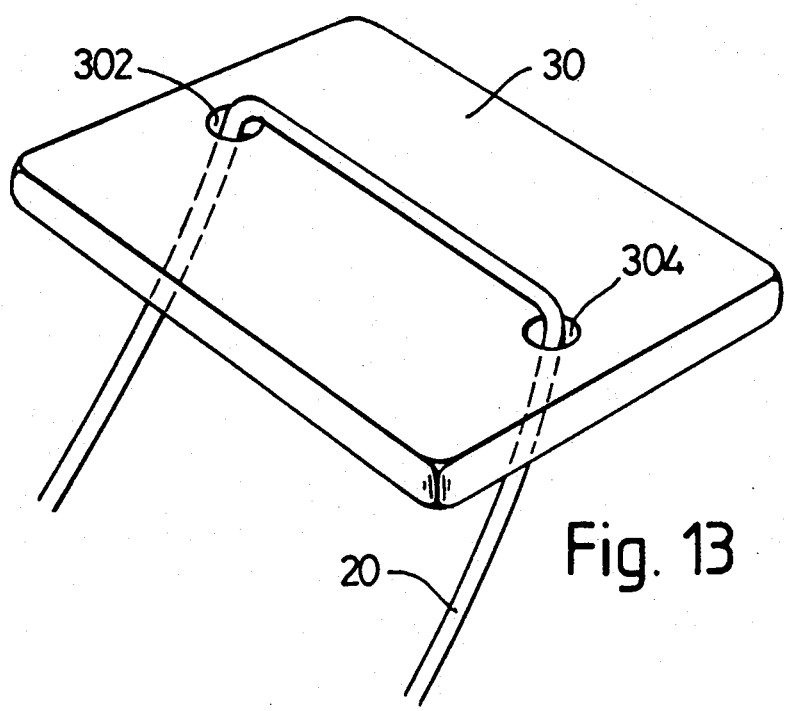
Figure 14:
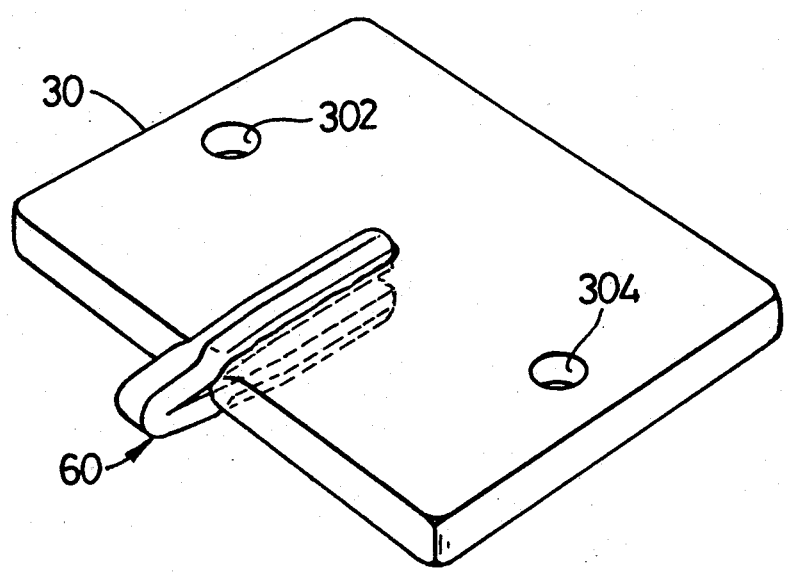

FIGS. 4 to 11 show sequentially the insertion of the suture apparatus into position, FIG. 12 shows a practical arrangement in which a second suture is placed in position to provide uplift for both sides of the urethra, FIG. 13 shows an alternative modified design of the pledget for use in accordance with the present invention, and FIG. 14 shows a metallic clip attached to a pledget according to the present invention to enable the position of the pledget to be determined by X-rays.

Figure 1:
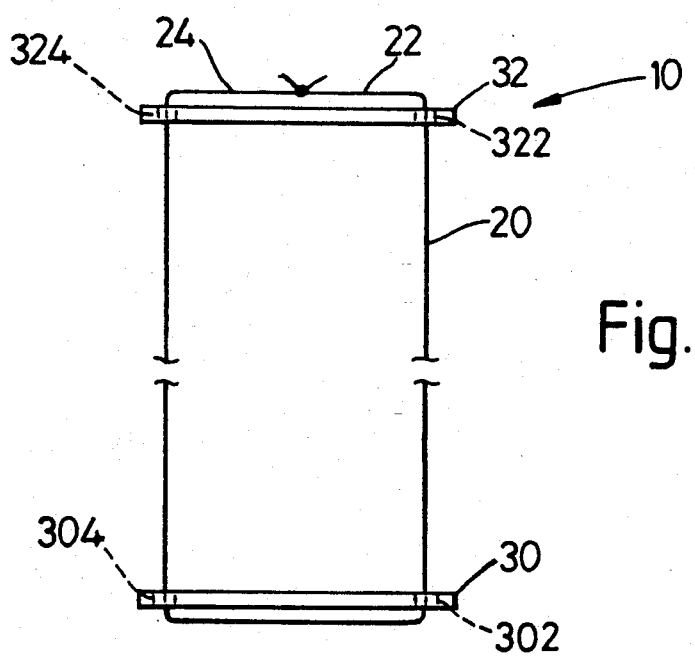
FIG. 1 shows schematically the suture apparatus according to the present invention.
Figure 2:
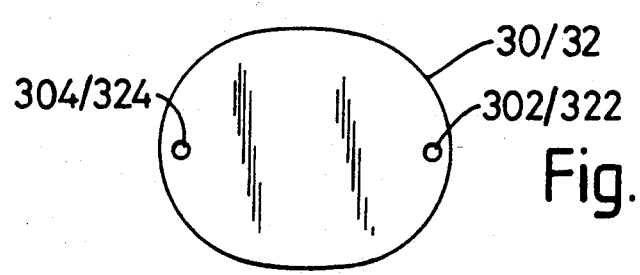
FIG. 2 shows a pledget for use in the apparatus of FIG. 1.

With reference now to FIGS. 1 and 2 the suture apparatus (10) comprises an elongate suture (20) and first and second pledgets (30, 32) which are preferably substantially identical.

Each pledget comprises a generally rectangular or oval plate which in a preferred embodiment is 12.5mm × 7mm × 2mm thick.

The suture is normally threaded through holes (302, 304) the bottom pledget (30) and is placed in a hermetically sealed package with the top pledget (32). Preferably (see also FIG. 12) two such identical sutures (20, 20') and pledgets (30, 32, 30', 32') are placed in a single hermetically sealed package.

Figure 3:
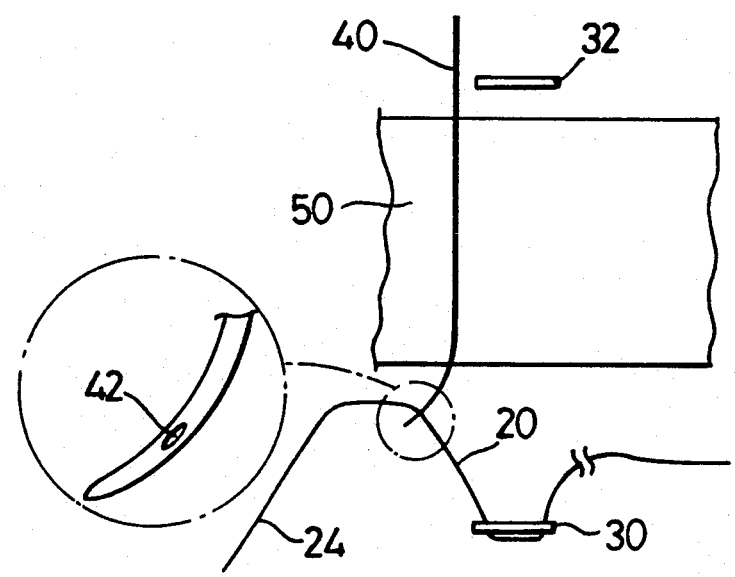
FIG. 3 illustrates the insertion method for the apparatus.

In use the suture (20) is threaded through holes (322, 324) in the top pledget (32) and the suture ends (22, 24) are tied as shown. The pledget (30) may be considered to be a bottom pledget and (see FIG. 3) the pledget (32) may be considered to be a top pledget. The end (24) of suture (20) is threaded into the eye (42) of an elongate needle (40) and the suture is pulled through the tissue (50) of a patient such that the suture emerges at the top end wherein the end (24) may be inserted through hole (324). A similar procedure is adopted for end (22).

The sequence of insertion is illustrated in FIGS. 3 to 12 for an operation known as the Stamey procedure which assists in alleviating conditions of incontinence in females.

Figure 4:
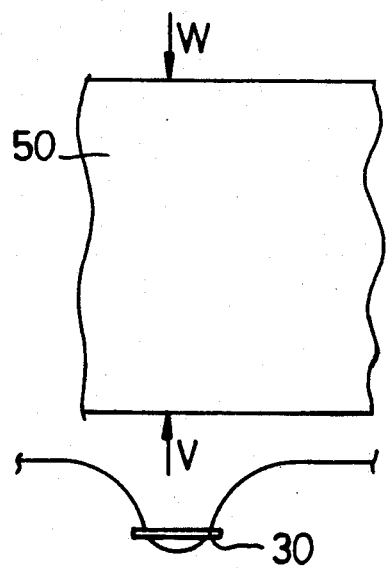
Figure 5:
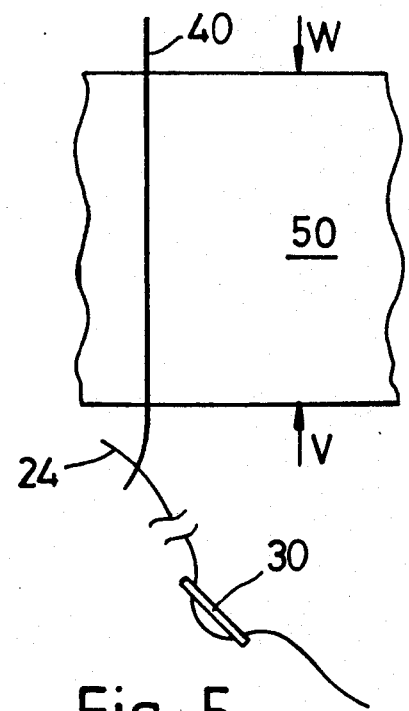

The tissue (50), illustrated diagrammatically, is between the rectus sheath of the outer abdominal wall (W) and the para-urethral tissue of the vaginal passage (V) (FIG. 4).

Figure 6:
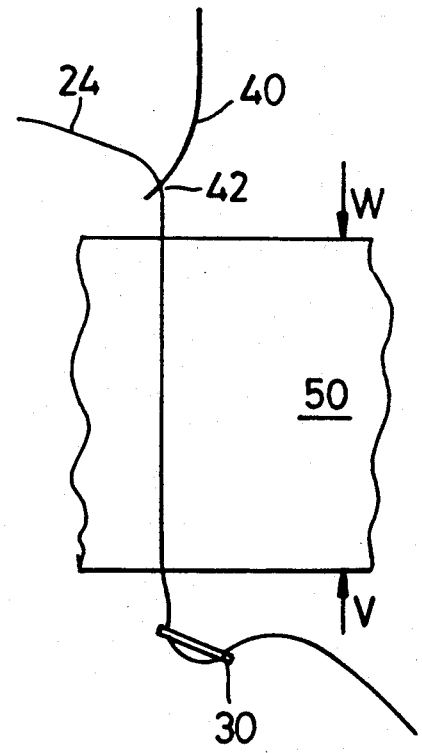
Figure 7:
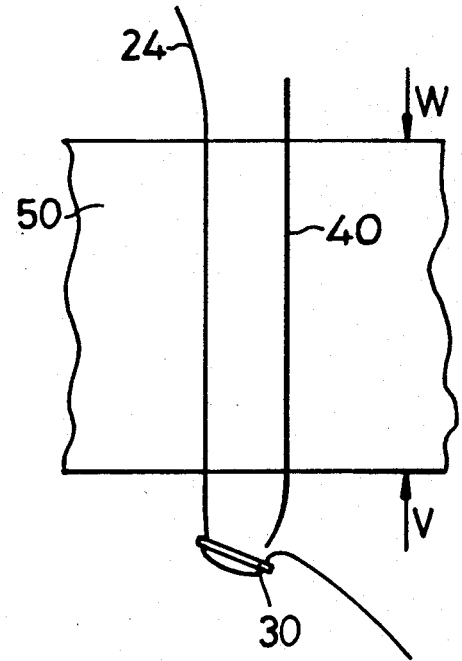
Figure 8:
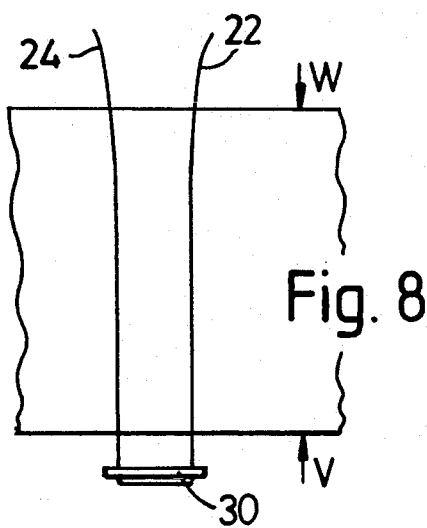

The already assembled bottom pledget (30) and suture (20) is inserted and (FIG. 5) an elongate needle (40) is pushed through the tissue (50) to a point of exit beside the urethra. One end (24) of the suture (20) is inserted into the eye (42) of needle (40) and the suture (20) is pulled up through the tissue to emerge as shown in FIG. 6.

Figure 9:
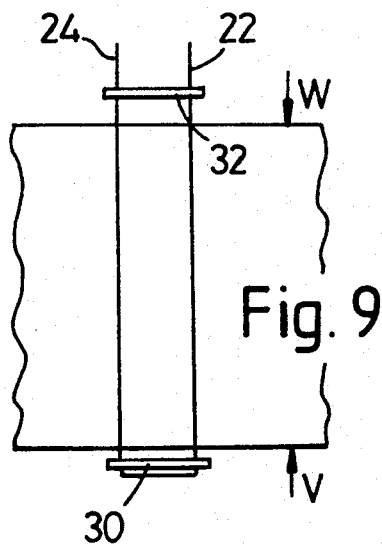
Figure 10:
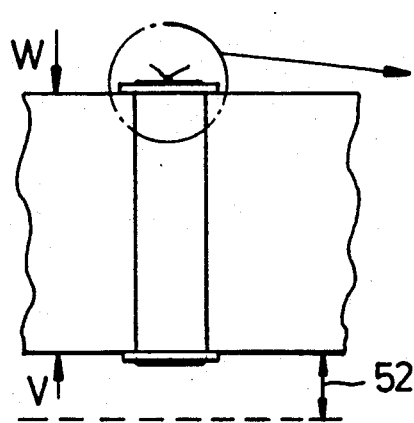

The elongate needle (40) is again inserted, a slight distance apart (FIG. 7) and the procedure repeated until (FIG. 8) both ends (22, 24) are protruding from the abdominal wall. The second (upper) pledget (32) is then positioned with ends (22, 24) of suture (20) threaded through the holes (322, 324) (FIG. 9). The ends (22, 24) are then tensioned to pull gently upwards on bottom pledget (30) such that tissue (50) is lifted by a distance (52).

FIG. 11 shows a detail of the upper pledget (32) being inserted beneath the skin (54) by placing it in an insertion (56). The upper pledget (32) therefore lies on the rectus sheath (58). The insertion may in known manner be stretched to conceal the top pledget (32) and suture ends (22, 24). At the bottom end a similar insertion is preferably made to enable the lower pledget (30) to be embedded in the para-urethral tissue (not shown) of the vaginal passage.

In practice, as shown in FIG. 12, a second suture apparatus (20', 30' 32') is then placed into position on the other side of the urethra to provide uplift for both sides.

The suture (20) may be non-stretchable or may be slightly elasticated. In the latter case this further assists in preventing damage from, for example, severe coughing.

The pledgets (30, 32) are shown as "rounded" rectangles (or straight sided ovals) to minimise damage to tissue. The pledgets may be made from radio-opaque material to show on X-rays. Dependent on their required use they may be made from bio-degradable material thus allowing them to dissolve after a predetermined period of time, as may the sutures. Generally however they will be non-absorbable for the above described operation thereby providing continuous relief.

If desired, the pledgets (30, 32) may be made from a material which absorbs tissue thus providing a firm support after a time.

The pledgets allow a good tension to be applied without much fear that they will be pulled through the tissue and therefore they allow substantial relief for incontinent persons.

In an alternative procedure the needle can be threaded from the vaginal incision to the abdominal incision thus reversing the roles of the pledgets.

A further practical form of a pledget (30) or (32) is shown in FIG. 13. This comprises a generally rectangular plate measuring in a preferred embodiment 12.5mm (½ inch) × 7.5mm (3/10 inch) × 1.5mm (6/100 inch) thick with holes (302, 304) 2.5mm (1/10 inch) in from each end. The rectangular plate preferably has rounded corners to prevent undue tissue damage. The suture is preferably approximately 80mm long with pledget (30) in the centre and two of these are preferably packed into a sterile package accompanied by two loose pledgets (20, 20') for the upper end (or in fact the lower end since as described above the procedures can be started either from the vaginal or abdominal approaches).

The pledgets are preferably made of TEFLON but could be made from other materials including DACRON/CARBON.

In a further modification shown in FIG. 14 a metal clip (60) may be placed on the TEFLON pledget (30) so that the pledget or pledgets on which such clips are placed become detachable on X-ray. This assists in determining their placement at a later stage, if for instance the patient's condition has deteriorated. A better judgement of cause can then be obtained.

A preferred clip is the standard WECK clip which is described in U.S. Pat. No. 4,188,953 and comprises a "V" shaped stainless clip made from round wire. The special existing applicator simply closes the clip around the pad or pledget as shown in FIG. 14. This clip being already in production and being already accepted for internal medical use is eminently suitable for this purpose. The pledgets (30, 32) will of course have to be non-absorbable to thereby ensure that the clip remains attached to the pledget.

When compressed the WECK clip comprises two parallel members and if squeezed hard on to the TEFLON pledget the clip will not protrude unduly. Thus there is virtually no further discomfort to the patient.

U.S. Pat. No. 4,188,953 includes a description of the clip both before and after application and by reference this is incorporated herein by way of explanation.

We claim:

1. A suture apparatus comprising an elongated length of suture, a first pledget comprising a first plate of bio-compatible material, the first plate being provided with a first and a second hole therethrough, the suture passing through the first and second holes to retain the first pledget in position on the suture, thereby providing a first end of said suture exiting from the first hole and a second end of the suture exiting from the second hole, a second pledget comprising a second plate of bio-compatible material, the second plate being provided with a third and a fourth hole therethrough, the third hole receiving in use the first end of the suture and the fourth hole the second end of the suture in which in use the first end of the suture passes through the third hole and in which the second end of the suture passes through the fourth hole for securing the two ends of the suture to the first and second pledgets, and a metal clip attached to at least one of the pledges to render the position of the at least one pledget determinable by X-ray.

2. A suture apparatus as claimed in claim 1 in which each pledget is radio-opaque being therefore viewable by X-ray.

3. A suture apparatus as claimed in claim 1 in which the suture is bio-absorbable.

4. A suture apparatus as claimed in claim 1 in which the pledgets are bio-absorbable.

5. A suture apparatus as claimed in claim 1 in which at least one of the pledgets is made from a material which allows tissue to grow therein to provide firmer anchorage for the sutures.

6. A suture apparatus as claimed in claim 1, in which each pledget comprises a substantially rectangular plate measuring approximately 0.5" × 0.3" × 0.06" thick with the holes in each plate being approximately 0.1" from the edge thereof.

7. A suture apparatus as claimed in claim 1 in which each pledget comprises a substantially rectangular plate measuring approximately 0.5" × 0.275" × 0.08" thick.

8. A suture apparatus as claimed in claim 1 in which each pledget comprises a substantially oval plate measuring approximately 0.5" × 0.275" × 0.08" thick.

9. A suture apparatus as claimed in claim 1 in which each pledget is made from TEFLON.

10. A suture apparatus as claimed in claim 1 in which the suture material is slightly elasticated providing a defined relative movement between the first and second pledgets.

* * * * *